US009380955B2

(12) United States Patent
Sanghera et al.

(10) Patent No.: US 9,380,955 B2
(45) Date of Patent: Jul. 5, 2016

(54) PATIENT SCREENING TOOLS FOR IMPLANTABLE CARDIAC STIMULUS SYSTEMS

(71) Applicant: CAMERON HEALTH, INC., St. Paul, MN (US)

(72) Inventors: Rick Sanghera, San Clemente, CA (US); Alan F. Marcovecchio, San Clemente, CA (US); James M. Keefe, Penn Valley, PA (US)

(73) Assignee: CAMERON HEALTH, INC., St. Paul, MN (US)

( * ) Notice: Subject to any disclaimer, the term of this patent is extended or adjusted under 35 U.S.C. 154(b) by 0 days.

(21) Appl. No.: 14/640,367

(22) Filed: Mar. 6, 2015

(65) Prior Publication Data

US 2015/0196211 A1    Jul. 16, 2015

Related U.S. Application Data

(63) Continuation of application No. 13/308,281, filed on Nov. 30, 2011, now abandoned, which is a continuation of application No. 12/196,779, filed on Aug. 22, 2008, now Pat. No. 8,079,959.

(60) Provisional application No. 60/957,456, filed on Aug. 23, 2007.

(51) Int. Cl.
*A61B 5/02*         (2006.01)
*A61B 5/0402*       (2006.01)
(Continued)

(52) U.S. Cl.
CPC .......... *A61B 5/0402* (2013.01); *A61B 5/04012* (2013.01); *A61B 5/04023* (2013.01); *A61B 5/6823* (2013.01); *A61B 5/742* (2013.01); *A61N 1/372* (2013.01)

(58) Field of Classification Search
CPC ............. A61B 5/0402; A61B 5/04012; A61B 5/04023; A61B 5/6823; A61B 5/742; G06F 19/3406
See application file for complete search history.

(56) References Cited

U.S. PATENT DOCUMENTS 4,023,276 A    5/1977 Furukawa et al.
4,030,486 A    6/1977 Eastman
(Continued)

FOREIGN PATENT DOCUMENTS

EP    1745741 A1    1/2007
WO    2007089959 A1    8/2007

OTHER PUBLICATIONS

Burri et al.; "Utility of the Surface ECG Before VDD Pacemaker Implantation," International Journal of Cardiology, vol. 117, No. 2, pp. 211-213; 2007.
(Continued)

*Primary Examiner* — Mallika D Fairchild
(74) *Attorney, Agent, or Firm* — Seager, Tufte & Wickhem LLP

(57) ABSTRACT

Tools and devices are provided for determining whether a patient is well suited to receiving an implantable cardiac stimulation device by analyzing cardiac signals captured using external or cutaneous electrodes. Some of the illustrative tools include shapes for visual comparison to printed ECG strips. Kits for use of illustrative tools are also shown. Automatic devices are also disclosed which perform at least some analytical functions electronically for a user. In an example, a printed ECG strip is visually compared to a shape in order to ensure a patient is well suited to receiving a cardiac stimulation device having a particular implant location and/or cardiac signal analysis method implementation.

20 Claims, 13 Drawing Sheets

(51) Int. Cl.
    *A61B 5/04*     (2006.01)
    *A61B 5/00*     (2006.01)
    *A61N 1/372*     (2006.01)

(56) References Cited

U.S. PATENT DOCUMENTS

| | | |
|---|---|---|
| 4,103,425 A | 8/1978 | Harter |
| 4,550,502 A | 11/1985 | Grayzel |
| 4,884,345 A | 12/1989 | Long |
| 5,137,025 A | 8/1992 | Turner, II |
| 5,987,352 A | 11/1999 | Klein et al. |
| 6,470,893 B1 * | 10/2002 | Boesen .......... 128/899 |
| 6,496,715 B1 | 12/2002 | Lee et al. |
| 6,647,292 B1 | 11/2003 | Bardy et al. |
| 6,721,597 B1 | 4/2004 | Bardy et al. |
| 7,149,575 B2 | 12/2006 | Ostroff et al. |
| 7,248,921 B2 | 7/2007 | Palreddy et al. |
| 7,330,757 B2 | 2/2008 | Ostroff et al. |
| 7,376,458 B2 | 5/2008 | Palreddy et al. |
| 7,404,256 B1 | 7/2008 | Parker |
| 7,421,300 B2 | 9/2008 | Smits |
| 7,496,409 B2 | 2/2009 | Greenhut et al. |
| 8,079,959 B2 | 12/2011 | Sanghera et al. |
| 8,565,878 B2 | 10/2013 | Allavatam et al. |
| 8,588,895 B2 | 11/2013 | Sanghera et al. |
| 2002/0169484 A1 | 11/2002 | Mathis et al. |
| 2007/0123947 A1 | 5/2007 | Wenger et al. |
| 2007/0239220 A1 | 10/2007 | Greenhut et al. |
| 2007/0276445 A1 | 11/2007 | Sanghera et al. |
| 2007/0276447 A1 | 11/2007 | Sanghera et al. |
| 2007/0276452 A1 | 11/2007 | Sanghera et al. |
| 2008/0172100 A1 | 7/2008 | Sanghera et al. |
| 2008/0188901 A1 | 8/2008 | Sanghera et al. |
| 2008/0269813 A1 | 10/2008 | Greenhut et al. |
| 2009/0093731 A1 | 4/2009 | Palreddy et al. |

OTHER PUBLICATIONS

International Search Report and Written Opinion for PCT/US2008/074118; issued Mar. 2009.

All non-patent literature documents and foreign patent documents have been previously uploaded in parent U.S. Appl. No. 13/308,281.

* cited by examiner

Shape too Small / Peak too Large     Shape too Large / Peak too Small

PATIENT SCREENING TOOLS FOR IMPLANTABLE CARDIAC STIMULUS SYSTEMS

RELATED APPLICATIONS

The present application is a continuation of U.S. patent application Ser. No. 13/308,281, filed Nov. 30, 2011, which is a continuation of U.S. patent application Ser. No. 12/196,779, published as US Patent App. Pub. Number 2009-0054796, titled PATIENT SCREENING TOOLS FOR IMPLANTABLE CARDIAC STIMULUS SYSTEMS, filed Aug. 22, 2008, which claims the benefit of and priority to U.S. Provisional Patent Application No. 60/957,456, filed Aug. 23, 2007, titled PATIENT DISCRIMINATION TOOLS FOR IMPLANTABLE CARDIAC STIMULUS SYSTEMS, and the disclosure of which is incorporated herein by reference.

FIELD

The present invention relates to the field of implantable medical devices. More particularly, the present invention relates to implantable cardiac stimulus devices and methods of determining whether patients are well suited to receive such devices.

BACKGROUND

Implantable cardiac stimulus devices (ICSDs) can be beneficially used to automatically detect malignant arrhythmias in patient cardiac function and deliver appropriate therapy. There are known indicators for determining whether a patient is susceptible to arrhythmias, and whether the patient is therefore likely to benefit from receiving an ICSD. For example, measurements of ejection fraction coupled with patient history can be used to determine whether a patient may benefit from implantation of an ICSD. Having identified a patient who needs an ICSD, the next step is to determine which of several ICSD options best suits the patient's needs. Tools for identifying patients who are well suited to certain ICSDs are desired.

SUMMARY

The present invention, in an illustrative embodiment, is directed toward a method for determining whether a particular patient is well suited to receiving a particular ICSD. In an example, a pre-operative patient screening tool is provided including a stencil designed for comparison to a printed ECG. The stencil provides indicia of how a particular ICSD detects cardiac events. Cutaneous electrodes are applied to the patient's skin and ECG signals are captured from the patient using the cutaneous electrodes to generate a printed ECG. The printed ECG is then compared to the stencil by aligning the stencil with the onset of a QRS complex in the printed ECG. If the QRS complex and a portion of the trailing signal fall within the area defined by the stencil, the QRS complex passes, indicating that the patient is likely well suited to the particular ICSD. One or several QRS complexes may be tested. Tools or kits for performing such methods are included as further embodiments.

In another embodiment, the present invention comprises a programmer for use with an ICSD. The programmer is configured to include inputs for attachment to electrodes that can be placed on the skin of a patient. The programmer can be activated to cutaneously capture ECG signals from the patient and may determine whether the patient is well suited to receive a particular ICSD. In another embodiment, the programmer may determine which of several possible ICSDs the patient is well suited to receive. In a further embodiment, a testing device that is not a fully functional programmer may be used to capture and automatically analyze a patient's ECG in a similar fashion. The programmer or testing device may be configured to emulate filtering that an implanted device would perform on captured signals. Methods associated with such programmers and testing devices make up further embodiments.

DETAILED DESCRIPTION

Figure 1:
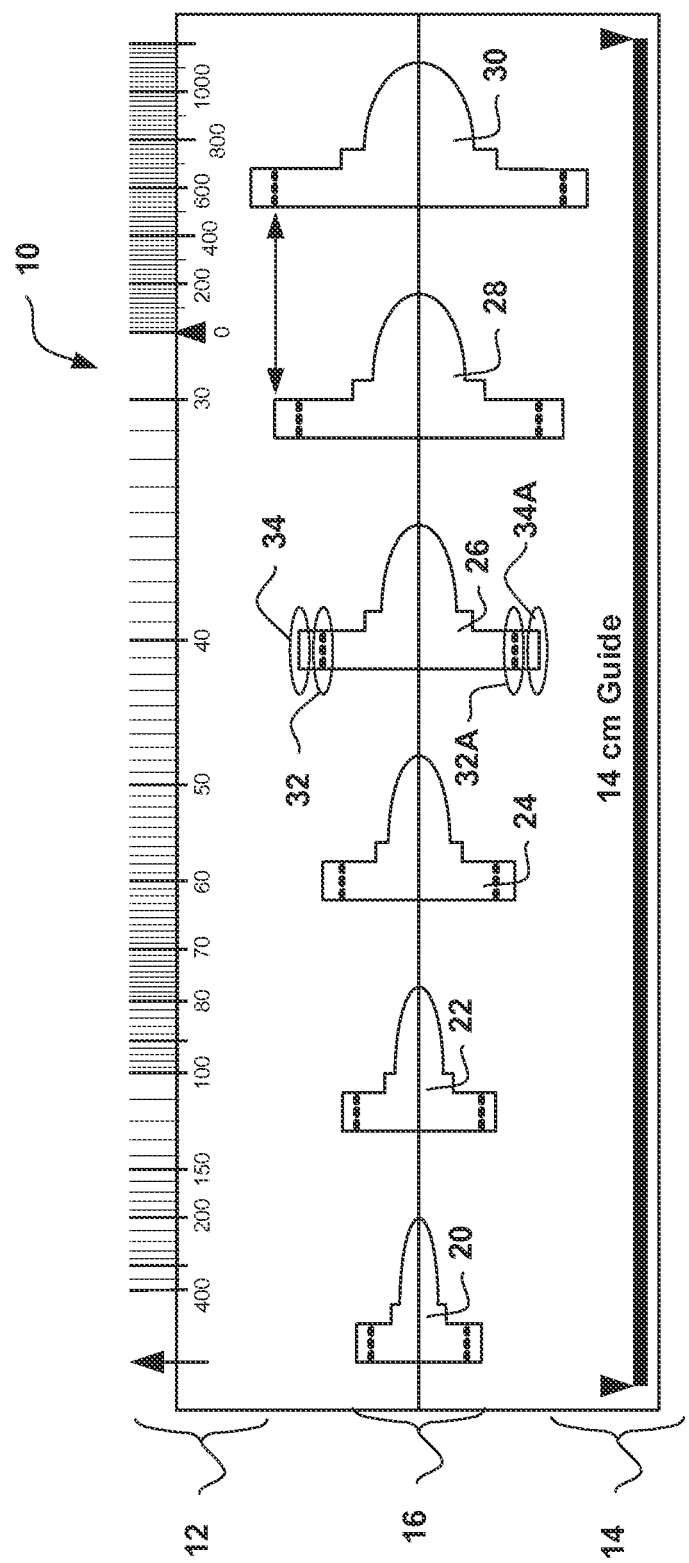
FIG. 1 shows an illustrative patient screening tool.

The following detailed description should be read with reference to the drawings. The drawings, which are not necessarily to scale, depict illustrative embodiments and are not intended to limit the scope of the invention.

As used herein, a practitioner or user may be a physician, a physician's assistant, a medical technician, a nurse, or any other person performing or assisting in performing any method or using any device or system disclosed herein. Also as used herein, a stencil refers to a visual aid including one or more patterns or shapes used for determining whether a potential implant recipient's cardiac signal is well suited to certain detection methods or devices.

An illustrative example includes a method for determining whether a particular patient is well suited to receiving a particular ICSD. In the example, a pre-operative patient screening tool is provided including a stencil designed for comparison to a printed ECG. In an illustrative embodiment, the stencil provides indicia of how a chosen ICSD detects cardiac events. Some embodiments make use of other solutions to patient screening, for example, as discussed below with reference to FIGS. 11-12.

In an illustrative example, cutaneous electrodes are applied to the patient's skin at locations corresponding to implant locations for a set of subcutaneous sensing electrodes that would be used in a particular ICSD. ECG signals are captured from the patient using the cutaneous electrodes to generate a printed ECG. The surface ECG can be used in this analysis as a surrogate for the subcutaneous ECG.

In the illustrative example, the printed ECG is compared to the stencil by aligning an appropriately sized shape in the stencil with the onset of a QRS complex (or, alternatively, some other signal feature such as the R-wave or T-wave peak) in the printed ECG. If the QRS complex and a portion of the trailing signal fall within the shape defined by the stencil, the QRS complex passes, indicating that the patient may be well suited to the particular ICSD. If a portion of the QRS complex and/or trailing signal falls outside the shape, then the electrode pair that generated the QRS complex is found to indicate poor suitability for a given location and patient posture.

NG. 1 shows an illustrative example of a patient screening tool 10. The patient screening tool 10 may be printed on a transparent plastic sheet, for example. The particulars of making the screening tool 10 can vary.

The patient screening tool 10 includes a rate scale shown at 12. The rate scale 12 can be used to estimate the rate of a patient's ongoing cardiac rhythm by aligning a QRS complex from a printed strip with the vertical arrow near the left edge of the rate scale 12 and determining where the second QRS complex to the right of the aligned QRS complex appears on the scale. In an example, a practitioner is instructed to perform patient screening when the patient's heart rate is in a predefined range, for example, less than 120 beats per minute, and to use a predetermined printing rate (such as 25 mm/sec) for printing the ECG. The suggestion to screen at only selected rates may be omitted, if desired.

A spacing guide is provided as shown at 14. The spacing guide 14 can be used to provide indicia for assisting in the correct placement of cutaneous electrodes on the patient to correlate with subcutaneous electrode positions. In the embodiment shown in FIG. 1, the screening tool is adapted for use with a subcutaneous-only ICSD similar to that shown in FIG. 2.

Figure 2:
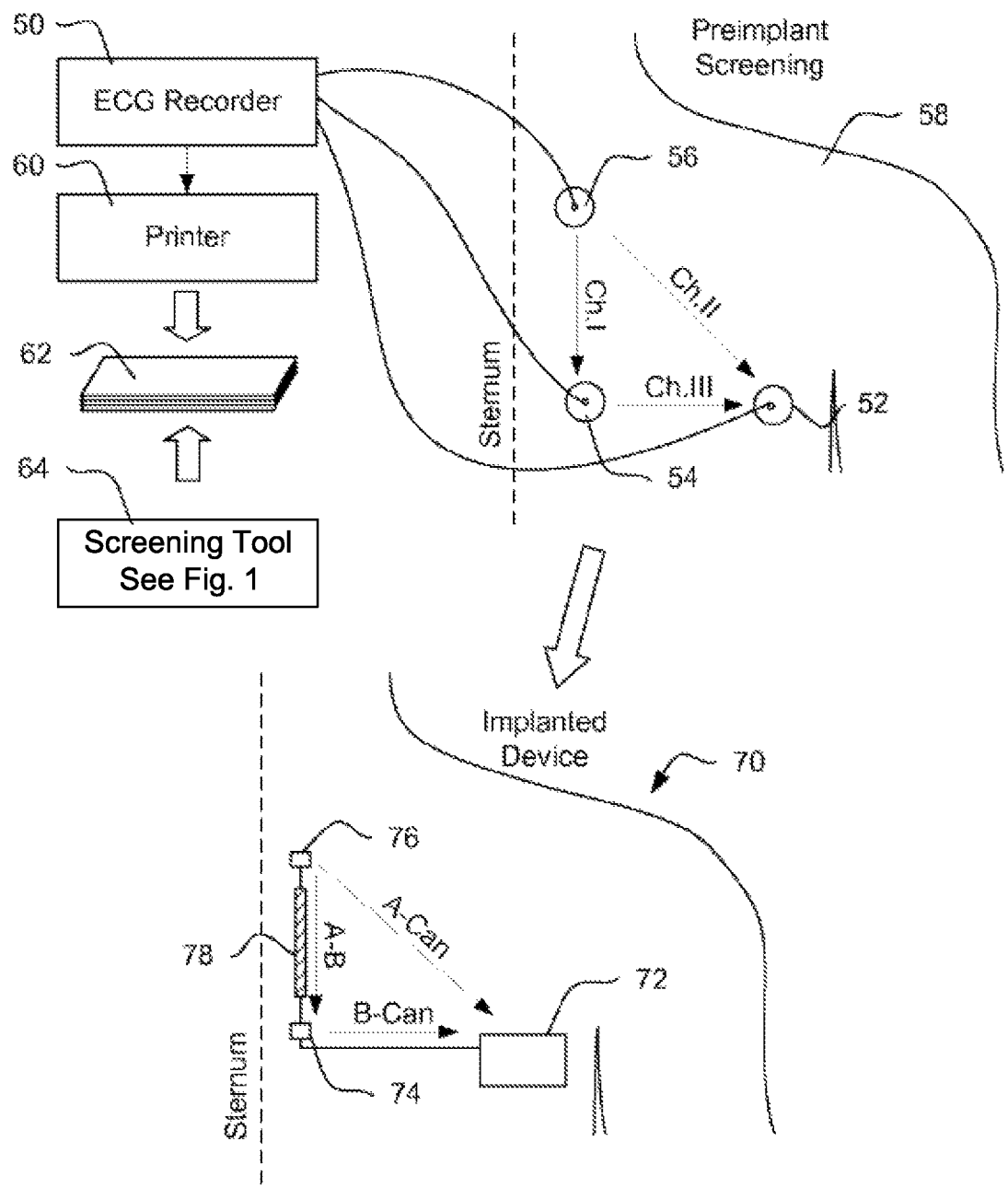
FIG. 2 pictorially illustrates a patient screening method.

Referring briefly to FIG. 2, a canister 72 is implanted in a lateral pocket and a lead extends medially from the canister 72. When the lead reaches the sternum, near the xiphoid, it is directed toward the head of the patient. In the example, the method places electrodes 74, 76, 78 along the left side of the sternum. In one such system, a first sensing electrode 74 is disposed 1-2 cm above and to the left of the xiphoid of the patient, and a second sensing electrode 76 is disposed about twelve cm above (superior to) the first sensing electrode 74 using incisions placed about fourteen cm apart. In the illustrative example of FIG. 1, the spacing guide 14 is shown as a "14 cm Guide" to enable identification first of the incision location, allowing correct placement of the cutaneous electrode near the incision location. Inclusion of a spacing guide 14 is optional.

The coil electrode 78 may also be used for sensing, if desired, and additional indicia for placing a corresponding cutaneous electrode may be included on the spacing guide 14 as well. If a spacing guide 14 is included, other distances and placements may be used; the 14 cm Guide simply illustrates one embodiment but should not be viewed as limiting.

Referring again to FIG. 1, the patient screening tool 10 also includes a stencil 16. The stencil 16 includes a number of shapes 20, 22, 24, 26, 28, 30 disposed along an alignment line shown across the center of the patient screening tool 10. Though not shown in FIG. 1, in a working example the individual shapes are not only outlined, but each is uniquely colored.

The shapes 20, 22, 24, 26, 28, 30 are sized such that each can be used for a particular range of ECG amplitudes by providing dashed lines to indicate minimum QRS amplitudes for each shape 20, 22, 24, 26, 28, 30. For example, the widest boundaries of shape 24 align with the dashed lines 32 and 32A of shape 26, and the widest boundaries 34 and 34A of shape 26 match the dashed lines for shape 28. If the peak amplitude of an aligned QRS does not fall within spaces between 32 and 34 or between 32A and 34A of shape 26, then shape 26 is not used. Thus, the dashed lines provide amplitude guidelines for using the shapes 20, 22, 24, 26, 28, 30. The shapes 20, 22, 24, 26, 28, 30 do not overlap in the illustrative example.

If a QRS is captured that does not meet the amplitude guidelines for any of shapes 20, 22, 24, 26, 28, 30, then the gain setting of the ECG monitor from which an ECG printout is received may be changed. For example, if captured QRS complexes are too big for shape 30, the ECG Recorderprinter gain would be lowered; conversely, if captured QRS complexes are too small for shape 20, the ECG Recorder/printer gain would be raised. However, the patient screening tool 10 may include instructions limiting the applicable gains. In an illustrative example, the user is instructed to use the patient screening tool only within a range of 5-20 mm/mV printed at 25 mm/second. This range may change depending upon the input parameters of the ICSD for which screening is being performed. If amplitude guidelines of the shapes 20, 22, 24, 26, 28, 30 cannot be met using an acceptable ECG gain setting, the patient screening test is failed for the pair of electrodes under consideration.

Figure 5A:
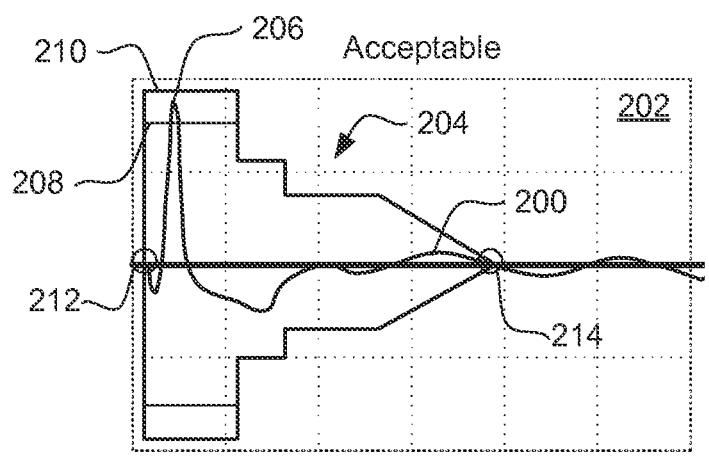
FIGS. 5A-5C illustrate comparisons of a patient screening tool shape to captured cardiac signals.
Figure 5B:
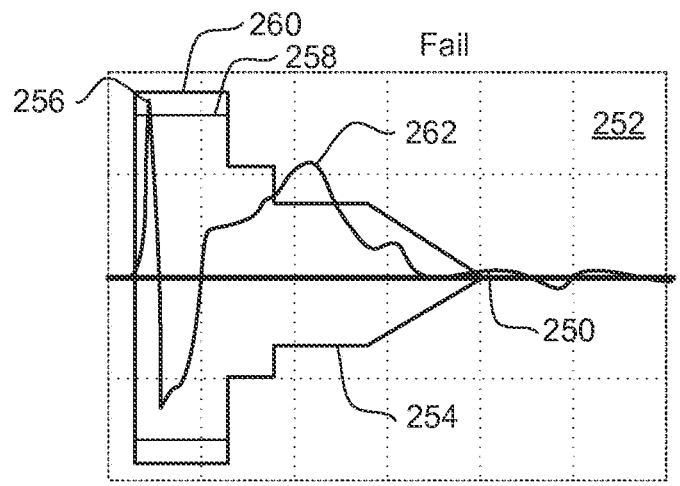
Figure 5C:
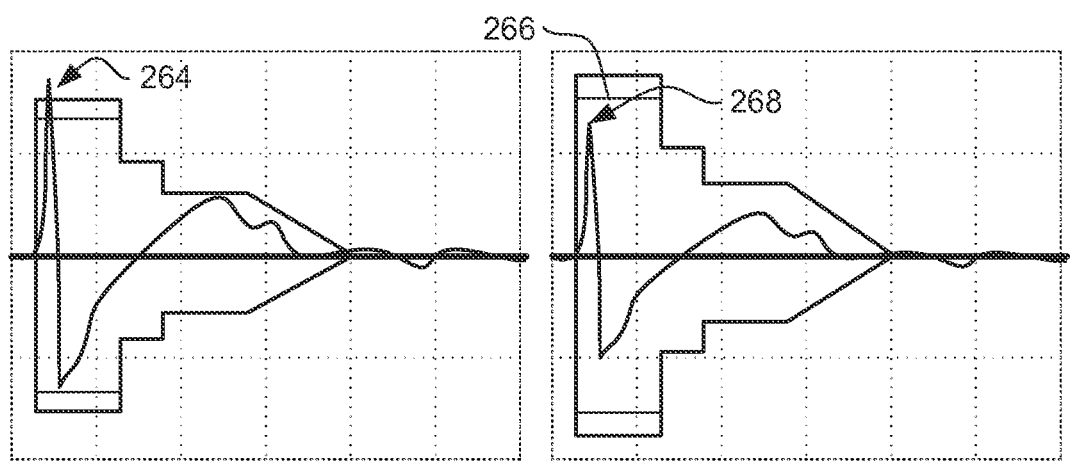

To determine whether a given patient is well suited to receive a particular ICSD, a correctly sized shape is compared to the printed ECG when it is aligned with a QRS complex, as shown below in FIGS. 5A-5C. FIG. 5A shows a QRS comparison that passes the patient screen, FIG. 5B shows a QRS comparison that fails the patient screen, and FIG. 5C shows incorrectly selected shapes. Briefly, a QRS fails if the trace crosses outside an appropriately sized shape 20, 22, 24, 26, 28, 30; otherwise, the QRS passes.

Whether the patient is found to be well suited to a particular device can be determined by one or several comparisons of QRS complex(es) to the stencil 16. In some embodiments, multiple measurements are performed by having the patient assume different postures (sitting, standing, supine, etc.) and testing the patient in each. This testing may be performed on one or several available sensing vectors for a particular ICSD.

In response to screening, a decision is made whether to implant the particular ICSD in the configuration for which testing was performed, or to use a different therapy (a different ICSD or a different configuration of the same ICSD, for example). It is envisioned that different testing tools 10 may be applied to test several ICSD systems and/or several configurations of a single ICSD until the patient passes, if possible.

FIG. 2 illustrates a process including both Preimplant Screening and an Implanted Device, in order to allow comparison of the two. Preimplant Screening is shown in which an ECG Recorder 50 is coupled to a cutaneous electrodes 52, 54, 56 that are placed on a patient 58. The ECG Recorder 50 is coupled to a printer 60 that is used to create printed ECG strips 62 for comparison to a Patient Screening Tool 64. If the patient 58 passes screening, an implant procedure is performed. The implantation, as completed following passing of the Preimplant Screening, is shown for a subcutaneous ICSD system 70.

The implanted system 70 is shown with a canister 72 placed along/below the inframammary crease at approximately the left axilla, with a first sensing electrode 74 disposed a few centimeters superior to and left of the xiphoid, with a coil 78 extending along the left side of the sternum about one-to-two centimeters to the left of the midline and a second sensing electrode 76 disposed superior to the coil 78. The implanted system 70 thus defines three sensing vectors, shown as A-Can, B-Can and A-B, where "A" indicates electrode 76, "B" indicates electrode 74, and "Can" indicates an electrode disposed on or that is defined as part of the canister 72.

The cutaneous electrodes 52, 54 and 56 are disposed on the patient 58 during preimplant screening to mimic a set of sensing vectors of the implanted system 70. Cutaneous electrode 56 corresponds to implanted electrode 76, cutaneous electrode 54 corresponds to implanted electrode 74, and cutaneous electrode 52 corresponds to an electrode on the implanted canister 72. As a result, the ECG Recorder receives a signal from Ch.I that correlates to the A-B sensing vector, a signal from Ch.II that correlates to the A-Can sensing vector, and a signal from Ch.III that correlates to the B-Can sensing vector. In one example, a standard ECG recorder is used with electrodes RA, LA and LL used as Ch.I, Ch.II and Ch.III, respectively.

The illustrative embodiment of FIG. 2 shows how one configuration of an implanted system may be tested with a patient screening tool 64. The patient screening tool 64 is shown in the format shown in FIG. 1. The comparison of the patient screening tool 64 to the printed ECGs 62 is further explained below by reference to FIGS. 5A-5C.

Figure 3:
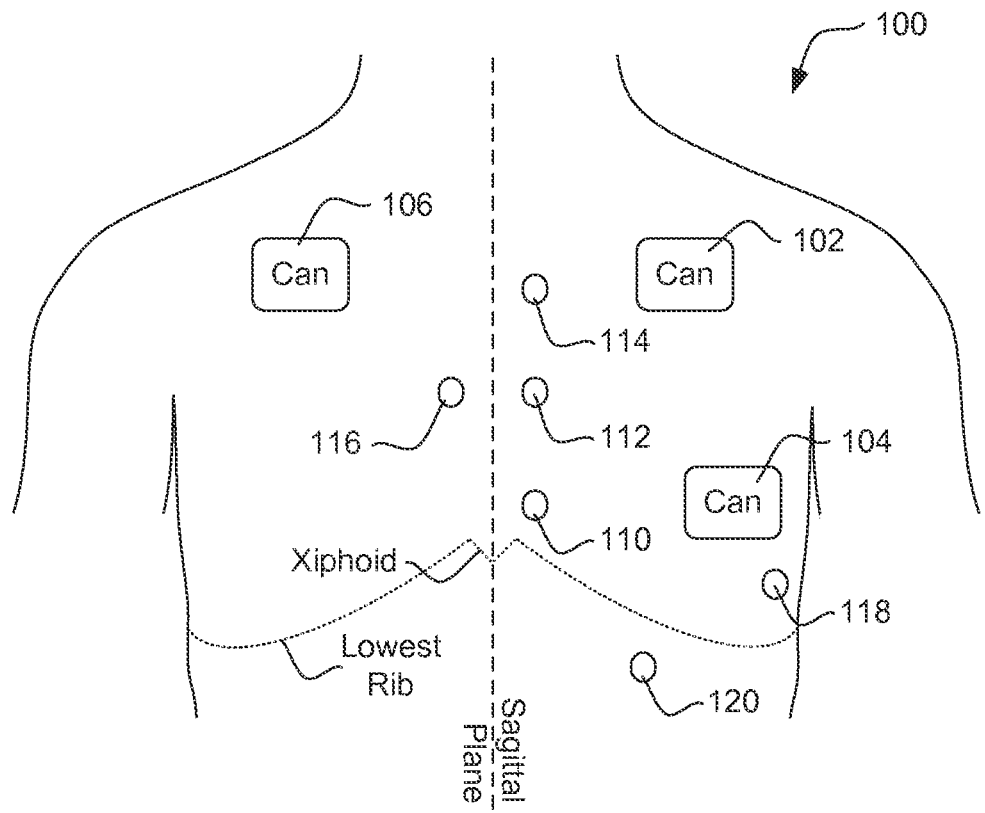
FIG. 3 shows various canister and electrode positions for subcutaneous implantation of an ICSD.
Figure 12:
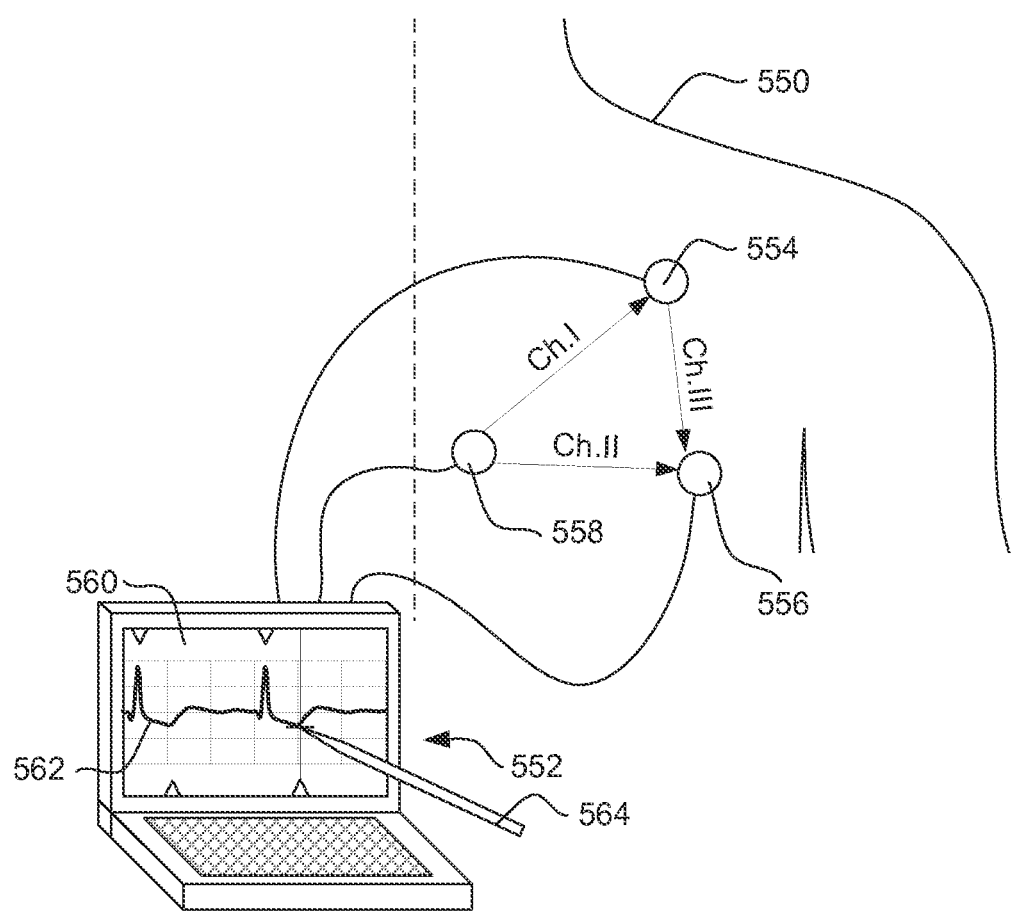
FIG. 12 shows yet another system for capturing data from a patient and providing feedback relating to patient suitability for an ICSD.

In some embodiments, multiple configurations may be tested, where, if a first configuration fails, a second configuration is tested. For example, if a first set of locations for the cutaneous electrodes 52, 54, 56 leads to a patient screening test failure, different locations for the cutaneous electrodes 52, 54, 56 may be selected, where each set of locations is based on distinct desired locations for different ICSD systems. For example, if the configuration as shown in FIG. 2 fails, a different set of locations such as shown in FIG. 12 may be tested. FIG. 3 shows several additional illustrative electrode locations. More than three cutaneous electrodes can be used in order to enable several configurations to be tested at once or for testing of more elaborate systems.

Figure 4:
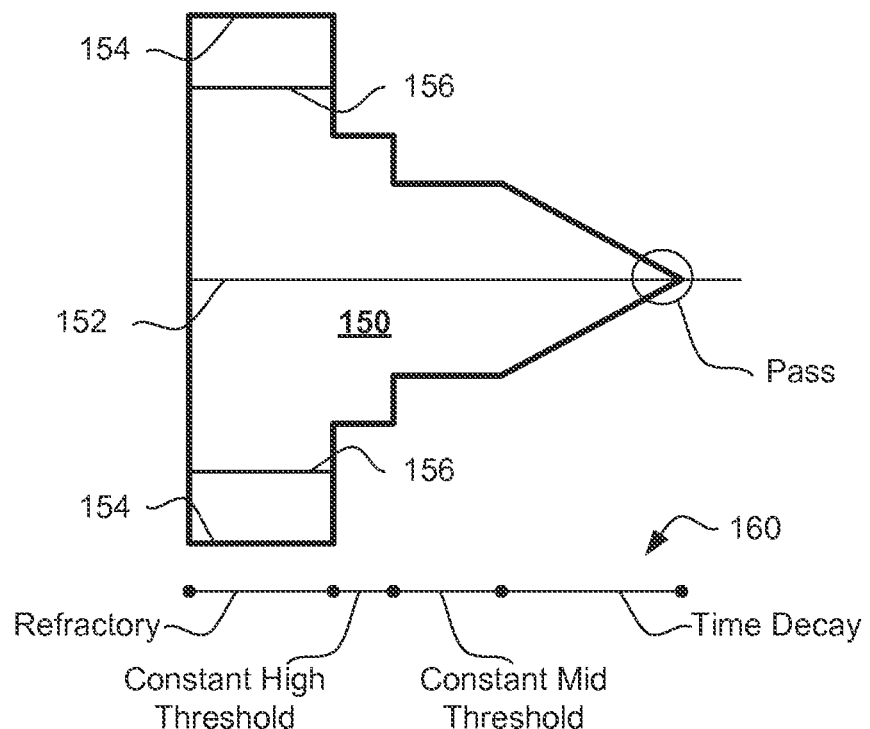
FIG. 4 shows an illustrative shape for a patient screening tool.

Details of the shapes on the patient screening tool 64 are further explained with reference to FIGS. 1 and 14. If there is a screening test failure for a first device configuration, a different screening tool 64 may be used to test an ICSD having a different cardiac signal analysis configuration. For example, the shape shown in FIGS. 1 and 14 may represent a first configuration for patient screening, while the shape shown in FIG. 4 represents a second configuration. The configurations may reflect different cardiac signal analysis methods used by different ICSDs and/or different programming choices in a single ICSD. For example, a system may have available programming for a first method for use with a patient having a relatively wide QRS complex and, also, programming for a method for use with a patient having a relatively large and/or late T-wave. If a first configuration fails preoperative screening, more configurations may be attempted until preoperative screening is passed, if possible. Variations may also be made in view of different sensing capabilities (such as differences in input circuitry) for different ICSDs.

While several embodiments disclosed herein determine whether a patient passes or fails a patient screening tool test, some embodiments may instead optimize the matching of a patient to a particular ICSD or ICSD configuration. Thus, rather than Pass/Fail, a screened configuration for a given patient may receive a grade indicating suitability, and, after screening two or more configurations, the "best" configuration may be selected for use.

In FIG. 2 the patient is shown as having received a subcutaneous-only system 70 having canister 72 and a lead electrode assembly 74, 76, 78. Additional illustrative subcutaneous systems are shown in commonly assigned U.S. Pat. Nos. 6,647,292, 6,721,597, and 7,149,575, and the disclosures of these patents are incorporated herein by reference. Unitary construction or multiple canisters/leads can be used in other embodiments, as desired.

Again in FIG. 2 the system 70 defines several sensing vectors shown as A-B, A-can and B-can. Upon implant, one of these sensing vectors may be selected as a default sensing vector. Some illustrative methods for sensing vector selection and/or device initialization are shown in commonly assigned copending U.S. patent application Ser. No. 11/441,522, published as US Published Patent Application Number 2007-0276445; U.S. patent application Ser. No. 11/441,516, issued as U.S. Pat. No. 7,623,909; U.S. patent application Ser. No. 11/442,228, published as US Published Patent Application Number 2007-0276452; and U.S. patent application Ser. No. 11/623,472, issued as U.S. Pat. No. 7,783,340, each of which is incorporated herein by reference. In other embodiments, multi-vector sensing may be performed.

In an illustrative example, screening analysis using a screening tool as in FIG. 1 is performed with steps for postural analysis as well. For example, the patient screening tool is applied to ECG signals captured with the patient in multiple postures to determine device suitability in each posture. Following implant, further analysis may be performed to incorporate postural change data into vector selection. For example, postural analysis of an implanted system 70 may be performed as discussed in commonly assigned and copending U.S. patent application. Ser. No. 11/672,353, published as US Published Patent Application Number 2008-0188901, which is incorporated herein by reference.

The canister 72 may house operational circuitry suitable for an implantable cardioverter/defibrillator. The operational circuitry may include, for example and without attempting to provide an exhaustive list, suitable memory, logic, analytical hardware, a microcontroller, batteries, antenna(e), charging circuitry, high-power capacitors, input/output circuitry, and telemetry circuitry. It is typical for the system 70 to be adapted to communicate with an external programmer (not shown) via known telemetry methods, to allow various functions to be performed, including device setup, status/history interrogation, new software upload, and/or detection/therapy modification. The details of the system 70 can vary widely.

Some illustrative methods for performing cardiac signal analysis are shown, for example, in commonly assigned. U.S. Pat. Nos. 7,330,757, 7,248,921, and 7,376,458, as well as commonly assigned U.S. Provisional Patent Application Nos. 61/034,938 and 61/051,332. Other methods are known throughout the art.

Some embodiments may include one or more transvenous leads having electrodes that can be placed and secured within an implantee's vasculature and/or heart or, alternatively, an intrathoracic lead having are epicardial electrode. These epicardial or transvenous leads may supplement or replace the subcutaneous lead shown in FIG. 2. A testing method using a stencil and shapes as shown may also be applied to screen patients fir a transvenous or epicardial system. For example, an appropriate surface model of cardiac signal analysis for a transvenous system can be used to design shapes/stencils for patient screening tools fir transvenous systems. The specifics of the implanted device and the analytical methods it uses can vary widely.

FIG. 3 shows a number of examples of canister and electrode positions for subcutaneous implantation of an ICSD. The illustrative systems are shown with canister positions including left pectoral/subclavicular 102, left lateral inframammary 104, and right chest 106. Several illustrative electrode positions are shown including left inferior sternum 110 (just above and to the left of the xiphoid), left medial sternum 112 (approximately over the ventricles) and left superior sternum 114 (approximately over or superior to the atria), as well as a right sternum position 116. Other positions away from the sternum may be used for placing an electrode, for example, a lateral subpectoral electrode 118. In addition to the anterior positions shown, posterior positions may be used including positions near the spine or near the scapula. Additional lateral positions may be used as well. A subcostal electrode 120 may also be used. Connections to the subcutaneous electrodes are not shown, but it should be understood that the lead(s) would be placed beneath the skin but over the ribs.

The locations shown are merely illustrative, and any desired combination of these positions may be used in a given device. Placement below or over the muscle will depend on implanting physician preference and/or patient anatomy; some positions (such as electrode 110) do not encounter significant muscle tissue. Additional examples may be found in commonly assigned U.S. Pat. No. 7,149,575, the disclosure of which is incorporated herein by reference. A hybrid system having multiple subcutaneous electrodes as well as a transvenous lead with one or more electrodes thereon may be used in another embodiment.

In one embodiment, a system is designed for use with several distinct sets of electrode locations. In an illustrative embodiment, preoperative patient screening is used to determine if any combination of the possible electrode locations provides suitable or even superior sensing, in order to determine whether and where the sensing electrodes can be placed. The pre-operative patient screening tool of FIG. 1 provides a visual reference for performing such screening quickly and easily.

FIG. 4 shows a shape 150 for use in a stencil on an illustrative patient screening tool. The illustrative shape 150 includes a baseline marker 152 for alignment with the baseline of a trace on a printed ECG strip. The shape 150 is selected such that the maximum deflection for a QRS complex is between a maximum amplitude line 154 and a peak indicator line shown at 156. The beginning of a QRS complex is aligned with the left side of the shape 150. As shown at 160, the widest portion of the shape 150 corresponds to the refractory period of a corresponding ICSD detection method, assuming that the ECG strip to which the shape 150 is compared is printed at a chosen sweep rate. For example, if a 160 ms refractory period is used in a corresponding implant device, the greatest amplitude portion 154 may have a length of 3.5 mm to enable use with ECG strips printed at a sweep rate of 25 millimeters per second. If the ECG falls outside the shape 150 during this first portion (FIG. 5C), shape 150 has been incorrectly selected and a different size should be chosen, if possible.

It should be noted that crossing the greatest amplitude portion 154 of the shape 150 in a "forward" direction, that is, through the right-most vertical line of the greatest amplitude portion 154 (due to long QRS width, for example), does not fail the amplitude requirement. Instead, a QRS that is sufficiently wide to cross the right-most vertical line of the greatest amplitude portion 154 indicates the QRS complex would fail the pre-implant screening itself.

To the right of this "refractory" portion of the patient screening tool shape, first and second constant threshold time periods occur, as indicated at 160, if the outer border of the shape 150 is crossed by the QRS and its trailing signal (which may include a T-wave, for example), then the screen will be failed. Following the high and mid constant threshold periods, the shape 150 is next defined by a time decay region. If the QRS and its trailing signal crosses the outer border of the shape 150 before it reaches the "Pass" area, which is shown illustratively with a circle in FIG. 4, the screen will be failed.

The "Pass" area is not narrowly defined, and some discretion may be used along this area. For example, a small crossing in the "Pass" area of shape 150 that appears to be caused by drift may be ignored. Alternatively, if an artifact of the patient's heart signal is identified, then crossing near the "Pass" area may be considered a screening test failure. The "Pass" area may be omitted in practice, for example, FIG. 1 is based on a working embodiment and lacks this detail.

FIGS. 5A-5C illustrate comparisons of a patient screening tool shape to captured cardiac signals. Referring to FIG. 5A, trace 200 is printed on ECG strip 202. The patient screening tool is placed on the ECG strip 202 such that shape 204 is generally aligned with the baseline of the trace 200. The shape 204 may include a line or other indicia for alignment with the baseline of the trace 200.

The trace 200 is shown as including a peak at 206. The shape 204 includes a peak indicator line shown at 208. The peak indicator line 208 is included to allow a user to determine that the shape 204 is sized correctly fir the trace 200. The shape 204 is correctly sized if the peak 206 falls between the outer line 210 and the peak indicator line 208 while the center of the shape 204 is aligned with the baseline of the trace 200. If this is not the case, a larger or smaller shape 204 can be selected from the patient screening tool.

The shape 204 is matched to the signal amplitude in this fashion to account for the use of an adaptive detection threshold that varies in response to the amplitude of incoming signals. For example, some detection methods use an estimate of peak amplitude to scale the detection thresholds up or down to achieve correct sensing. Thus, selecting a correctly sized patient screening tool accounts for changes in device event detection sensitivity that result from variation in signal amplitude.

In the example shown in FIG. 5A, the trace 200 represents an acceptable beat that passes the screening test because it does not cross outside of the border of the shape 204 until the end of the shape 204 as shown at 214. The test may be performed once, as shown, or it may be repeatedly performed on a number of captured beats of the trace 200. In some embodiments, different shapes may be used during this screening if the amplitude of the signal changes. However, in one illustrative example, a screening failure may be identified if the screening requires use of more than two shapes or use of shapes that are not adjacent in size (referring to FIG. 1, shapes 22 and 24 are "adjacent in size" while shapes 22 and 26 are not). If the trace 200 passes each time it is tested, then the trace 200, and a corresponding sensing vector and patient posture, pass preoperative screening. Several vectors and postures may be tested.

FIG. 5B shows a beat which fails preoperative screening. Here, the trace 250 is shown on ECG strip 252. A shape 254 from a patient screening tool is placed on the ECG strip 252 relative to the trace 250. The shape 254 is aligned with the baseline of the trace 250, and its size is selected such that the QRS peak 256 falls between the peak indicator line 258 and the outer line 260 of the shape 254. In this instance, the analyzed QRS complex includes a large T-wave shown at 262, which extends outside of the shape 254. Because a portion 262 of the trace 250 falls outside of the border of the shape 254, this signal fails to pass the test and may be marked as Poor or Failing.

In one illustrative example, if any captured event is marked as failing for the trace 250, the trace 250 and associated sensing vector or posture is marked as failing, in another example, further analysis may be performed in one of two ways.

First, further analysis may be performed to determine whether the signal, when analyzed in more detailed fashion, would be difficult to analyze for an ICSD of a particular configuration. This may include analyzing the ratio of the amplitude of the QRS peak to the T-wave peak or analysis of some other signal-to-noise ratio. Other factors such as the timing/spacing of noise may be considered including, for example, the O-T interval, the QRS width, or whether bigeminy is apparent. For example, further analysis of screening failures may reveal whether a method of identifying erroneous detection can be readily applied to a particular trace 250. This may include analysis using double detection identification methods, for example, as discussed in copending U.S. Provisional Patent Application No. 61/051,332.

Second, further analysis may be performed to determine whether the trace 250 consistently fails (i.e. a large percentage of QRS complexes fail). For example, if most QRS complexes fail, the sensing configuration would fail, while if some fail (for example, 5-10% or less), the sensing configuration is acceptable but less than ideal. If multiple configurations are tested, the "best" configuration may be selected.

FIG. 5C shows two examples of incorrectly selected shapes for the given traces. The shape on the left is incorrectly selected because the QRS peak falls outside of the widest region of the shape, as shown at 264. The shape on the right is incorrectly selected because the QRS peak is not large enough to meet the peak indicator line 266, as shown at 268.

The illustrative beat analysis shown in FIGS. 5A-5C may be performed in the clinical and/or ambulatory setting. For example, beats may be analyzed as captured while a patient is in a clinic. In some examples, a patient may receive a Holter monitor to wear for a period of time, and an ECG may be taken from data captured using the Holter monitor and that ECG can be analyzed. Portions of the captured data that are analyzed can be identified by observation of the beat rate for the patient, and events captured during one or both of high and low rate periods may be analyzed using patient screening tools.

Figure 6:
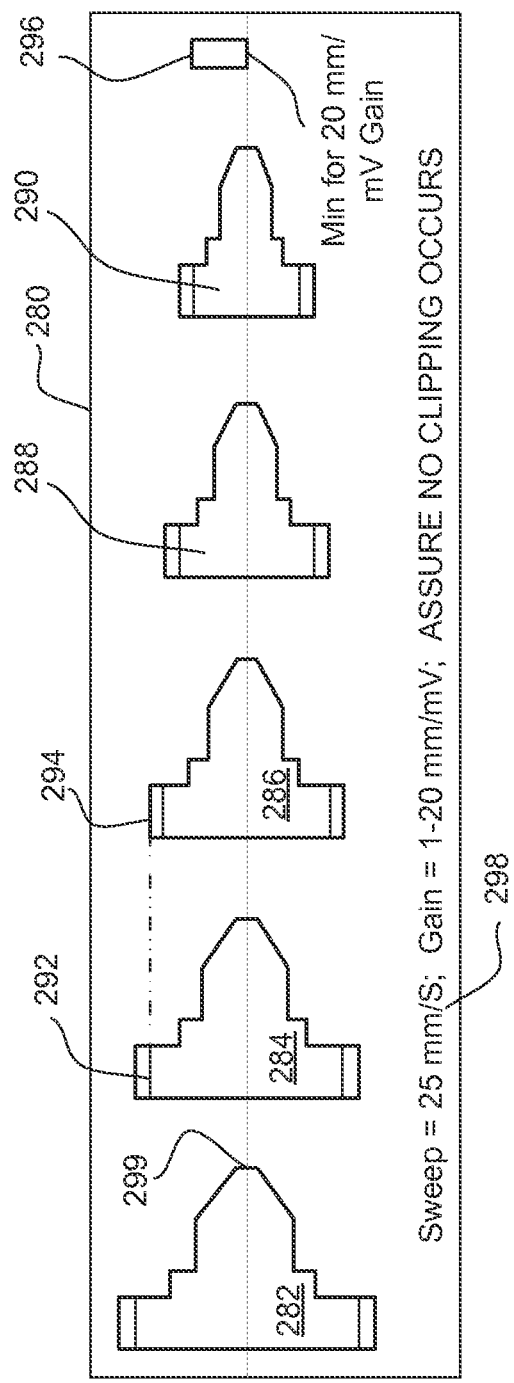
FIG. 6 shows a patient screening tool in the form of a transparency having several shapes thereon.

FIG. 6 shows a patient screening tool in the form of a transparency having a stencil with several shapes shown thereon. The screening tool 280 is shown as including several shapes 282, 284, 286, 288, 290 thereon. The differently sized shapes 282, 284, 286, 288, 290 are provided on the screening toot 280 to allow a practitioner to select the correct size shape for a given QRS complex. The screening tool 280 is designed such that the peak indicator 292 of a larger shape 284 matches the maximum amplitude portion 294 of the next smaller shape 286.

The screening tool 280 is also designed to assist in alignment, with a centered baseline displayed for alignment with the ECG strip. Each of the shapes 282, 284, 286, 288, 290 includes a "snub" nose shown at 299. When applied to a QRS, if the ECG trace exits the shape at the "snub" portion 299, this will be considered acceptable; crossing any other line of the shape would constitute a failure. The snub nose provides a clear indication of the "Pass" area noted in FIG. 4. The border of each shape may be displayed in any suitable fashion, and regions interior to and outside of the border may be differentiated, if so desired, in any suitable fashion, including shading, coloring, opacity, etc.

The screening tool 280 is shown with an amplitude test shape 296. The amplitude test shape 296 indicates the minimum acceptable signal amplitude given defined ECG parameters. Illustrative instructions for sweep and gain used by the ECG recorder and printer are shown at 298. As also indicated at 298, the gain may be adjusted, so long as there is no clipping or cutting off of the peaks of the signal. As indicated, the amplitude test shape 296 is useful when the highest allowed gain setting is applied by the ECG printing device. If a QRS printed at 20 mm/mV is not larger than the amplitude test shape, then the screening test is failed for that QRS.

Figure 7:
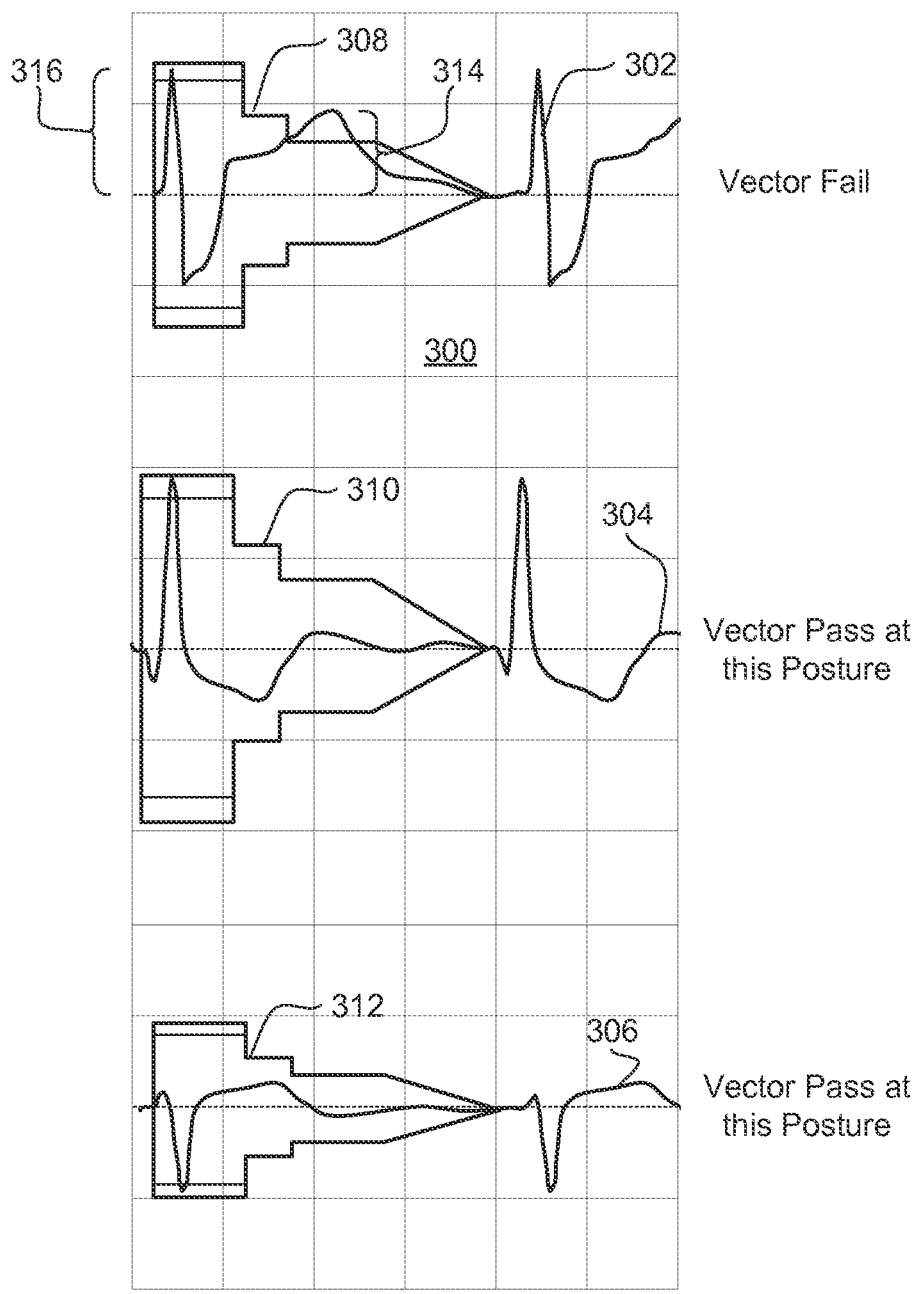
FIG. 7 shows shape comparison for several traces on a single ECG strip.

FIG. 7 illustrates comparison to three traces on a single ECG strip. The strip 300 includes a first race shown at 302, a second trace shown at 304, and a third trace shown at 306. The first trace 302 is compared to a first shape 308, the second trace 304 is compared to a second shape 310, and the third trace 306 is compared to a third shape 312. The shapes 308, 310, 312 are selected to match the greatest magnitude of the respective trace 302, 304, 306. Because each trace 302, 304, 306 varies in printed size, differently sized shapes 308, 310, 312 are chosen for each.

It can be seen that the first trace 302 fails because portions fall outside of the border of the first shape 308. The second trace 304 passes because it stays within the border of the second shape 310, and the third trace 306 also passes because it stays within the border of the third shape 312. In this scenario, the second trace 304 and the third trace 306 pass the screening test in the posture.

Figure 8:
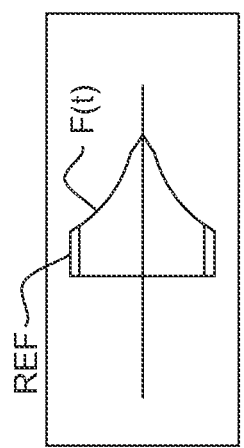
FIG. 8 shows another shape for use in a patient screening tool stencil.

FIG. 8 shows another shape that may be used in a patient screening tool. Rather than a stepped shape as shown in FIGS. 5-7, the shape in FIG. 9 includes smooth contours. Other embodiments may use different shapes as well, for example as shown in FIGS. 1 and 14.

In the shape shown in FIG. 8, a refractory period portion is shown at REF. This portion can be used to identify correct amplitudes for use with a given shape. Following refractory is a sloped time-decaying portion, F(t). F(t) may be shaped to match a time decaying threshold Th(t) taking this form:

$$Th(t)=X*\exp(r(t.\mathrm{sub.}0-t))+Y$$

Where X is an amplitude factor, r is a decay factor, t0 is the time at which the decay begins, and Y is the sensing floor.

Figure 14:
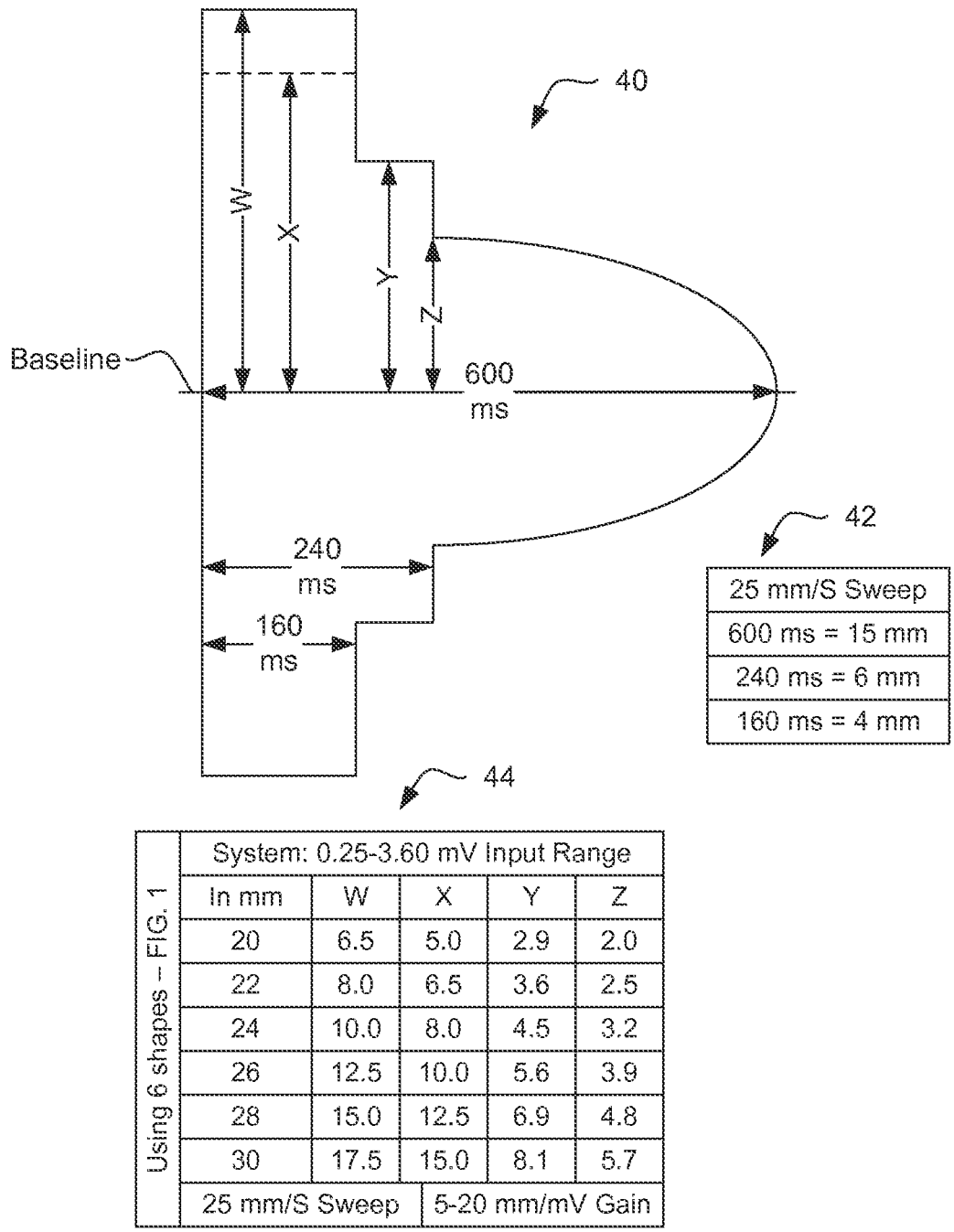
FIG. 14 provides details of a working embodiment for a patient screening tool as shown in FIG. 1.

FIGS. 1 and 14 provide alternatives to that shown in FIG. 8. Rather than sloping to match Th(t) as shown in FIG. 8, a bullet shape is used instead. This design is adapted to focus the screening tool analysis on the QRS complex and trailing T-wave, which both occur prior to the bullet-shaped portion of these shapes.

Figure 9:
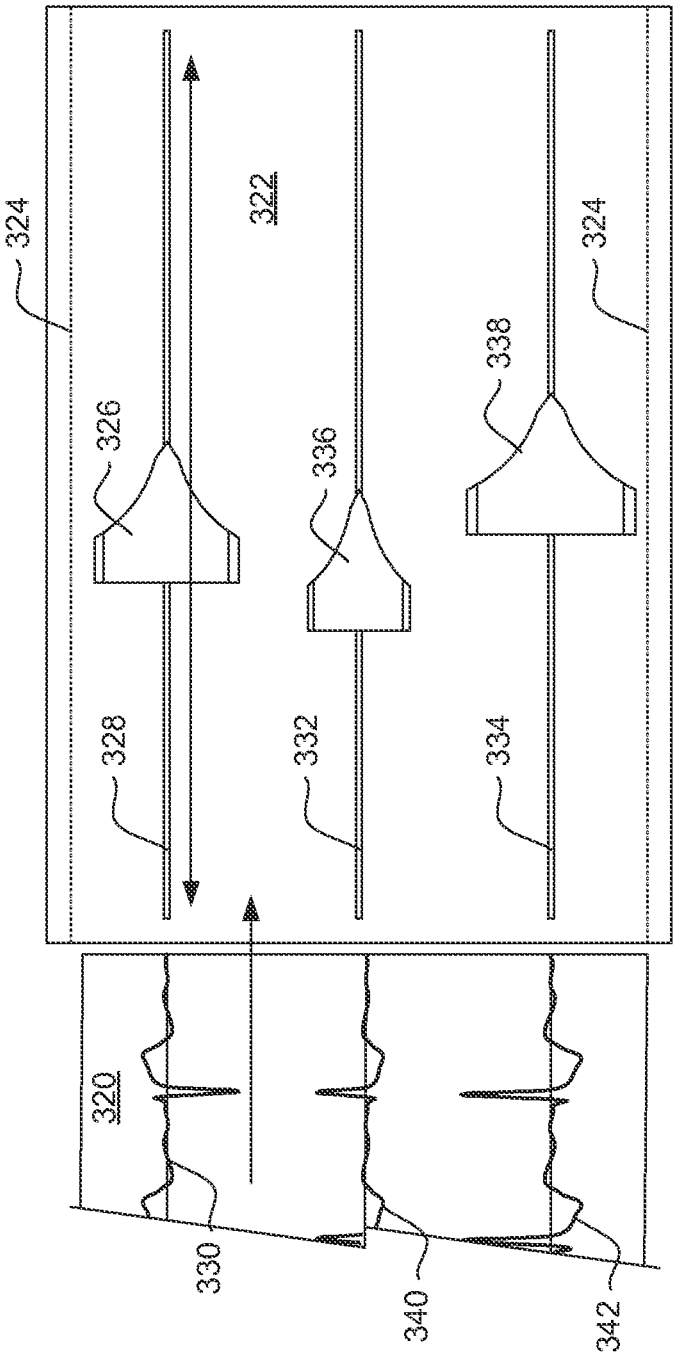
FIG. 9 shows a system having shapes for comparison to a printed three-trace ECG strip.

FIG. 9 shows a system having shapes for comparison to a printed three-trace ECG strip. For example, the system of FIG. 2 illustrates sensing vectors Ch.I, Ch.II, and Ch.III, and would be well suited to printing three traces side-by-side as shown on the strip 320. The strip 320 can then be inserted into a comparison tool 322 having guide edges 324 that align the strip 320.

A shape 326 is slidably secured relative to a track 328 in alignment with the baseline for trace 330. Additional tracks 332, 334 align shapes 336, 338 for comparison to traces 340 and 342. In some embodiments, the shapes 326, 336, 338 may be snap fit or magnetically secured onto a moveable element in the tracks 328, 332, 334, to allow exchange of different sized shapes 326. It can be seen that the three shapes 326, 336, 338 are each differently sized to accommodate the variation in amplitudes of the signals represented by the three traces 330, 340 and 342. In another embodiment, rather than snap fit, it is thought that the moveable elements for shapes 326, 336, 338 may be configured to increase or decrease in size as they slide to the left or right within tracks 328, 332, 334. Other designs for the system may be used, and those of skill in the art will readily recognize that the particulars, including the number of traces used and the manner of controlling comparison of the shapes 326, 336, 338 to the ECG strip may be changed in a number of ways.

In another embodiment, rather than moveable elements in tracks 328, 332, 334, side-by-side stencils each including a number of differently sized shapes may be included in a comparison tool. The stencils may be similar to that shown in FIG. 1 or 6, for example. An ECG strip would be advanced in the comparison tool until a QRS begins appropriately for a correctly sized shape. In another example, the stencils can be provided as cut-outs on the cover of the comparison tool 322, enabling a practitioner to mark individual QRS complexes as passing or failing as the strip is passed through the comparison tool 322.

Figure 10:
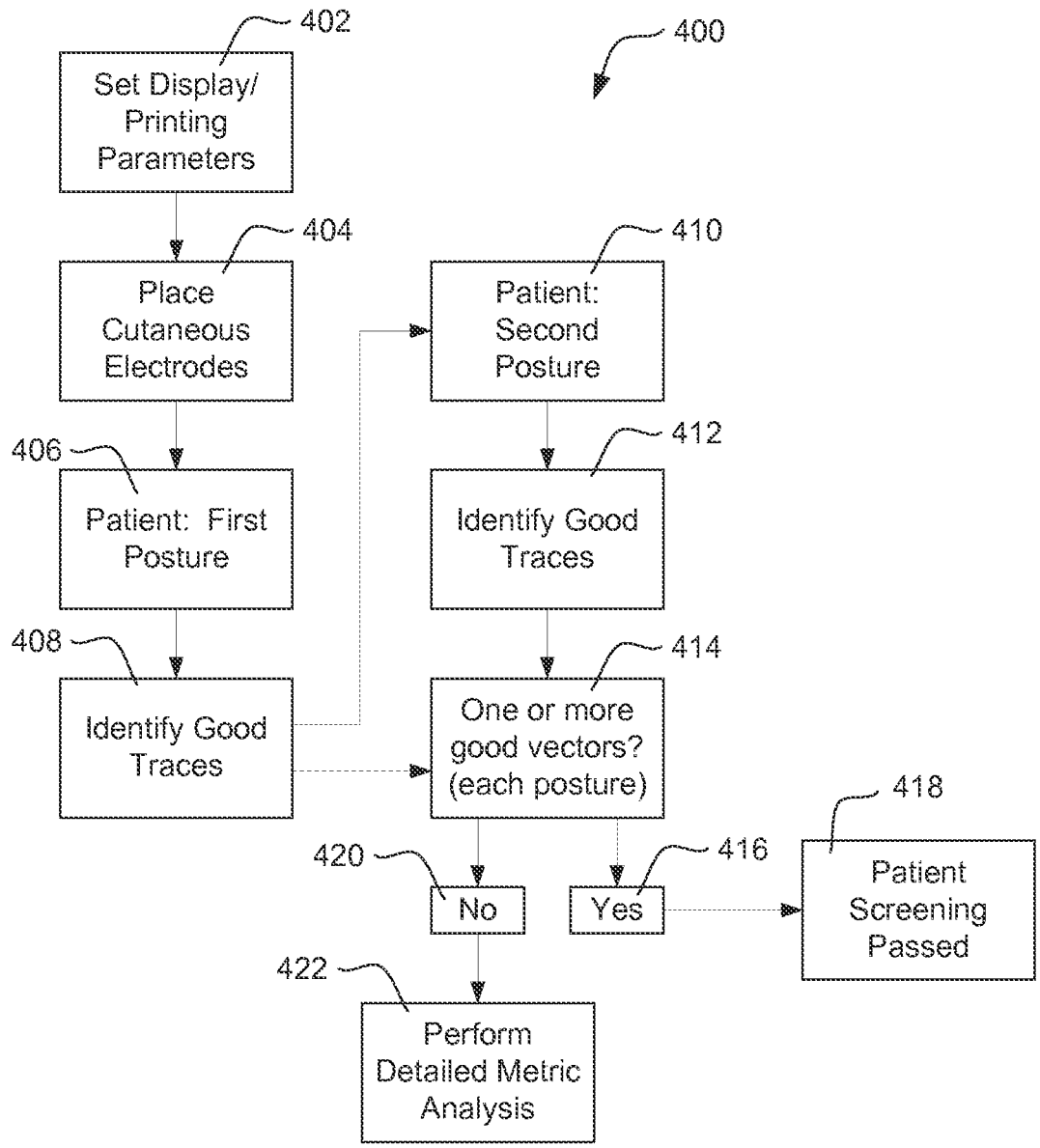
FIG. 10 is a block diagram for an illustrative method.

FIG. 10 is a block diagram for an illustrative method. The method 400 begins by setting display and/or printing parameters, as shown at 402. As noted above, a patient screening tool may include directions for sweep and gain that should be used for printing the ECG for use with a screening tool.

Cutaneous electrodes are placed as indicated at 404. The illustrative method next includes having the patient assume a first Posture, as shown at 406. These steps 402, 404, 406 may be performed in any order. Data is captured and one or more Good traces, if any, are identified, as shown at 408. A "Good" trace is one which passes patient screening by comparison of printed ECG data to a patient screening tool.

The patient is then directed to move into a second Posture, as shown at 410, and any Good traces are again identified, as shown at 412. For example, two or more postures (selected, for example, from standing, supine, prone, sitting, lying on left or right side, etc.) may be used. Optionally, the assessment of multiple postures may be skipped in some embodiments, with the method 400 advancing from step 408 directly to block 414. In yet another embodiment, data capture may be performed with an ambulatory patient while the patient performs some predetermined activity, such as walking, or, in another method, while the patient is sleeping, by using a Hotter monitor to acquire data in a non-clinical setting. In yet another embodiment, data from each posture for each vector may be captured, and following completion of data capture, the individual vectors and postures are each analyzed.

At block 414, a determination is made whether there are one or more "Good" vectors. This may be determined by analysis of results for each posture used. For example, for a patient in whom three traces are tested in two postures, the following data may result:
TABLE-US-00001 Posture\Vector Ch. I Ch. II Ch. III Supine Poor Good Good Standing Good Poor Good
If at least one vector is "Good" in each posture, then the query at 414 results in a Yes 416 and the patient screening is passed. For example, using the above table, vector Ch.III would cause the patient screening to be passed. If, in contrast to the above, every vector is "Poor" or fails in at least one vector, the query at 414 results in a No 420 and detailed metric analysis is performed, as shown at 422.

Detailed metric analysis 422 may include numerical analysis of signal-to-noise ratio, overall amplitude, etc. This may include analysis of one or more of the following for at least one cutaneous sensing electrode pair while the patient is in at least one posture: [0082] Analyze QRS width and compare to threshold; [0083] Analyze Q-T interval and compare to threshold; [0084] Calculate signal-to-noise ratio (SNR) and compare to a threshold; [0085] Calculate average or minimum amplitude and compare to threshold; [0086] Combine SNR and amplitude to generate a score to compare to threshold; [0087] Assess timing data for noise peaks and cardiac beat peaks; and/or [0088] Peak and/or SNR variability data may be considered.

In addition, the calculations performed in U.S. patent application Ser. No. 11/441,522, published as US Published Patent Application Number 2007-0276445; U.S. patent application Ser. No. 11/441,516, issued as U.S. Pat. No. 7,623,909; U.S. patent application Ser. No. 11/442,228, published as US Published Patent Application Number 2007-0276452; U.S. patent application Ser. No. 11/672,353, published as US Published Patent Application Number 2008-0188901; and U.S. patent application Ser. No. 11/623,472, issued as U.S. Pat. No. 7,783,340, each of which is incorporated herein by reference, may also be performed to analyze signal quality for signals captured cutaneously.

In yet another embodiment, a patient who does not pass the pre-implant screen is not further analyzed and instead fails the screening rather than undergoing detailed numerical analysis. A patient who fails screening for a given ICSD may be instructed to receive a different device, or may be screened for a different ICSD or different ICSD configuration.

Figure 11:
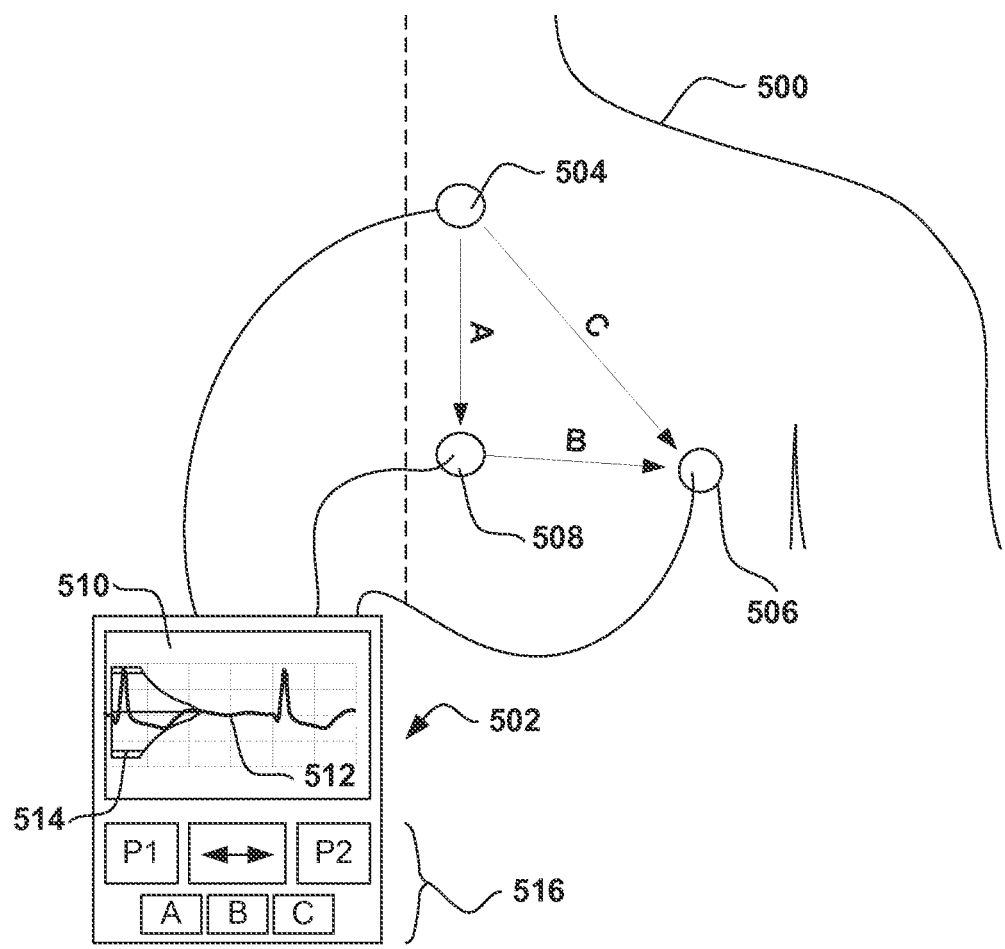
FIG. 11 shows another system for capturing data from a patient and providing feedback relating to patient suitability for an ICSD.

FIG. 11 shows another system for capturing data from a patient and providing feedback relating to patient suitability for an ICSD. A patient 500 is subject to analysis using an external device 502 coupled to external cutaneous electrodes 504, 506, 508, defining vectors A, B and C. The position of the cutaneous electrodes 504, 506, 508 is merely illustrative of locations that could be used for the lateral canister, left parasternal lead assembly location as shown above in "Implant" in FIG. 2. Other locations may be used in other embodiments, including other anterior positions and/or anterior posterior combinations such as shown in FIG. 3 and/or with implanted transvenous leads in a hybrid system.

The external device 502 may resemble a personal digital assistant (PDA), for example, and may be a general purpose device running specialized software, or it may be a dedicated device. If desired, the external device 502 may also be a programmer for an implantable device. The internal electronics and processing circuitry may include a power supply such as a battery or a circuit for receiving power from a plug-in, in addition to such memory and/or processing circuitry (such as a microprocessor) as may be suitable for performing its functions. As shown, the external device 502 includes a display screen 510, which may or may not be a touch screen. On the display screen 510 a trace is shown at 512, and, optionally, a comparison shape is shown at 514. The shape 514 may be chosen from a menu in order to match amplitude to a captured event, although in some embodiments the shape 514 is automatically sized to match event amplitude by the processing circuitry of the external device 502.

Showing the shape 514 on the display is optional, as the device 502 may itself perform signal processing to determine suitability of one or more sensing vectors. If internal processing/analysis is performed by the device 502, user input may be requested as a matter of last resort, for example, to resolve uncertainty in the analysis by asking the user to identify QRS complexes.

Controls shown at 516 may be used to control the display screen 510 and/or analysis. For example, buttons P1 and P2 may be used to indicate whether/when the patient 500 has assumed a desired posture and is ready fir testing/observation, while buttons A, B, and C may be used to select a channel corresponding to one of the available sensing vectors A, B, C for display or analysis.

The trace 512 may be shown in real time, or stored data may be shown on the display screen 510. The arrow button may be used to move or pause the trace 512 on the display screen 510. These buttons are merely illustrative, and less, more, or different buttons may be provided. The use of the term "button" should not be construed as limiting to a particular structure; any suitable structure for allowing user input may be used, including a touch screen or a microphone for receiving voice commands.

The use of the display screen 510 may allow a practitioner to show to the patient 500, for example, how the trace 512 compares to the shape 514. The device 502 may have additional outputs for communication (wireless or wired) to a server, computer, additional display, printer, removable storage media, etc. The display screen 510 may be used to direct a practitioner and patient through steps of the process, including, for example, directing the practitioner to use predetermined locations for the electrodes 504, 506, 508 and/or directing the practitioner and patient through a series of predetermined postures (sitting, standing, prone, supine, etc.) during data captured and/or analysis.

The device 502 may perform analysis of the sensing vectors A, B and C and provide an indication to a practitioner of suitability and/or, if desired, which vectors are well suited to use. More than three electrodes may be used, if desired, and placed cutaneously at locations corresponding to locations for implant electrodes, allowing a practitioner to identify and/or select electrode implantation sites. Further, multiple configurations could be tested to identify "best" locations for a given patient.

The device 502 may include input circuitry that is configured to mimic input characteristics, such as filtering, of an implantable device. For example, implantable devices may include various filters that are useful to exclude DC offset and external noise (including myopotentials from patient muscle contractions as well as 50/60 Hz line noise). In some embodiments, device 502 may include filtering circuits to mimic analog filtering of an implantable device and/or device 502 may include digital filtering circuitry (or may incorporate a digital filter into a microprocessor) to either copy or mimic models of implantable device(s). This may improve the accuracy of measurements with device 502.

FIG. 12 illustrates a device allowing for more detailed analysis by marking signal and/or noise peaks. Patient 550 is coupled to a programmer 552 using cutaneous electrodes 554, 556, 558, which are placed for observing signal suitability in a configuration using a pectoral canister location and dual leads (not shown) extending to a left parasternal location and a lateral inframammary location. The screening device is shown as a programmer 552, while in other embodiments, a non-programmer external device, which may take any suitable form, may be used instead. Three sensing vectors are defined at Ch.I, Ch.II, and Ch.III.

The programmer 552 allows a practitioner to use one device for each of patient suitability testing, implantation and subsequent follow-up interrogation. The illustrative embodiment in FIG. 12 illustrates the use of a stylus 564 to identify features of a displayed trace 562 on the touch screen 560. For example, a practitioner may perform analysis using the displayed trace 562, rather than manually marking a printed ECG strip Once marked on the touch screen 560, analysis of signal-to-noise ratio, noise timing, amplitude, etc. may be performed automatically by the programmer 552. This function may also be incorporated into a non-programmer, for example, a device as shown in FIG. 11.

Again, any suitable number of electrodes 554, 556, 558, may be used, and other locations than those shown may be tested. The marking of the ECG trace on the touch screen could also be performed without the patient present, for example, data could be downloaded from a Holler monitor, locally or over the Internet or a dedicated system, or data could be captured while the patient is in a clinical setting and then analyzed after the patient is gone or otherwise disconnected from the analysis device. Further, the programmer 552 could itself perform the marking of QRS complexes for the trace 562.

In yet a further embodiment, the programmer 552 can apply about detection method that would be used by an implanted device and the practitioner can use the stylus 564 to mark the detected beats as true or false detections. The programmer 552 tracks the marking of true and false detections and determines whether the beat detection method in combination with the locations of the electrodes 554, 556, 558 results in suitable cardiac signal analysis.

As with each embodiment shown above, rather than wired connections to the electrodes 554, 556, 558, wireless coupling may be provided for this analysis.

Figure 13:
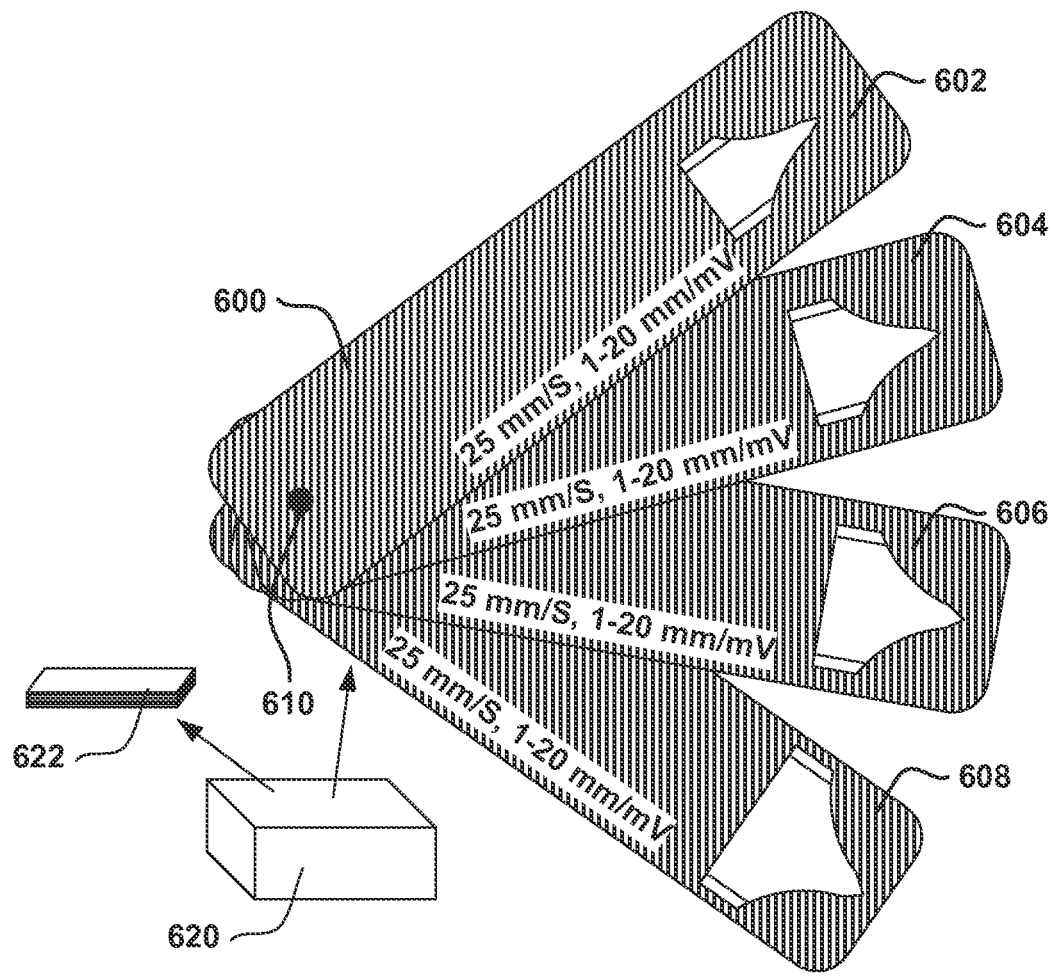
FIG. 13 shows another illustrative embodiment allowing a user to select from among several available patient screening tools.

FIG. 13 illustrates another embodiment in which several differently sized patient screening tool shapes are available. The tool 600 includes several strips 602, 604, 606, 608 that can be moved about an axis 610 to allow one of the strips 602, 604, 606, 608 to be selected. As indicated, each strip 602, 604, 606, 608 provides instructions to a user for the proper setting of ECG printout or display equipment. The illustrative tool 600 is configured with clear stencil/shape regions surrounded by a patterned field.

The illustrative tool 600 is shown as being packaged in a kit 620 along with instructions 622. Similar kits 620 may be use to provide any of the illustrative embodiments of patient screening tools (such as in FIGS. 1, 2, 6, 9 and 13) and/or devices (such as in FIGS. 11-12). Alternatively the patient screening tool 600 may be provided as part of a larger kit for an overall system, or may simply be provided to practitioners with training and reminders on the tool itself as in FIG. 1.

Referring to FIG. 14, a functional embodiment will be described. This embodiment was designed for use with a subcutaneous-only ICSD having an input voltage range of up to 3.6 millivolts, with a noise floor estimated in the range of about 80 microvolts. Based on a selected 3.times. signal to noise floor ratio, the smallest allowable peak amplitude was set at 0.25 millivolts.

Given the above sensing parameters, a screening tool having the six shapes 20, 22, 24, 26, 28, of FIG. 1 was selected. These shapes were sized as shown in FIG. 14. Timing features were as shown at the reference shape 40. The times are translated into actual lengths in table 42, which indicates the sizing is set up for use at a 25 mm/S sweep rate. The dimensions for references W, X, Y and Z are shown in millimeters in table 44.

For this illustrative example, the allowed gains for ECG printing were set to 5-20 mm/mV. Thus, for example, the largest amplitude would be found using the largest "W" value and dividing by the smallest gain. Thus, at 5 mm/mV, with W=17.5 mm, 3.5 millivolts was the largest QRS that would be allowed. This leaves a margin of 0.1 millivolts to prevent clipping by the implant. The smallest amplitude would be found using the smallest X value (the amplitude minimum) divided by the largest gain. Thus, at 20 mm/mV, with X=5.0, the smallest input would be at 0.25 millivolts.

The numbers are designed to allow full coverage of a major portion of the available dynamic input range of a corresponding ICSD. The example shown does not call for overlap of the shapes. If desired, some overlap may be allowed by letting the peak indicator lines overlap the outermost edges of adjacent shapes. For example, referring to FIG. 1, peak indicator lines 32, 32A could correspond to smaller amplitudes than the maximum amplitude for shape 24, while maximum amplitude 34 of shape 26 could be wider than the peak indicator lines on shape 28.

The above examples focus primarily on pre-implant screening. Post-implant testing may also be performed. In at least one illustrative example, a cutaneous testing system may be used to analyze or debug device operation after an implantation is complete. For example, following implantation, cutaneous testing may be performed by placing cutaneous electrodes at locations corresponding to subcutaneous electrode locations of an implanted device. The detection characteristics of the implanted system may be compared to signals observed or generated cutaneously to identify sensing flaws in an implanted system. In particular, lead failures may be diagnosed by this method/system, although other problems with input or detection circuitry or methods, for example, may also be analyzed. If used in this fashion, at least one of the cutaneous electrodes may double as, or may be attached using a lead that incorporates an antenna for communication with the implanted system. One or more cutaneous electrodes may also incorporate a magnet for disabling therapy response of the implanted system during the external analysis.

While much of the above is explained in the context of a subcutaneous cardiac signal capture system, shape comparisons may also be based upon intracardiac or intravascular data. For example, data may be gathered during an electrophysiology study. Data may also be captured from an implanted device having transvenous and/or epicardial electrodes, for example, using data relayed via telemetry to an external device. The shape comparison may also be performed to determine suitability of a hybrid device having subcutaneous and/or intravascular or intracardiac electrodes.

In some embodiments, several different patient screening tools may be used for several different device configurations. In an alternative embodiment, one patient screening tool may integrate shapes adapted to each of several cardiac signal analysis methods. For example, the shape may include different semi-transparent regions of color, for example, visually indicating whether one or more of these features are identified in the trace. Thus the patient screening tool may be used to identify whether any of several available detection methods for a particular ICSD would be suitable.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A patient screening device for use in determining whether a patient is well suited to receiving an implantable cardiac device (ICD) having a first configuration, the patient screening device comprising:
   a user interface allowing for user input and display of information to a user;
   inputs for coupling to a plurality of cutaneous electrodes; and
   operational circuitry configured to emulate filtering and detection characteristics of the ICD of the first configuration;
   wherein the operational circuitry is configured to perform a method comprising:
   capturing data via the inputs from coupled cutaneous electrodes placed on a patient;
   emulating the filtering and detection characteristics of the ICD of the first configuration, including applying a beat detection method that would be used by the ICD of the first configuration;
   determining whether the ICD of the first configuration can accurately analyze cardiac data from the patient and:
   if the ICD of the first configuration can accurately analyze cardiac data from the patient, determining that the patient is well suited to receiving the ICD of the first configuration; or,
   if the ICD of the first configuration is not likely to accurately analyze cardiac data from the patient, determining that the patient should not receive the ICD of the first configuration.

2. The patient screening device of claim 1, wherein, if it is determined that the patient should not receive the ICD of the first configuration, the patient screening device is configured to further analyze the data captured from the patient using emulation of the filtering and detection characteristics from an ICD of a second configuration to determine whether the patient is well suited to receive the ICD of the second configuration.

3. The patient screening device of claim 1, wherein the operational circuitry is configured to use the user interface to direct a user as to a correct location of cutaneous electrodes on the patient during testing for the ICD of the first configuration.

4. The patient screening device of claim 1, wherein the operational circuitry is configured to use the user interface to direct a user to instruct the patient to adopt at least a first posture and a second posture during the step of capturing data.

5. The patient screening device of claim 1, wherein the device is a programmer configured to perform follow-up evaluation of the ICD of the first configuration.

6. The patient screening device of claim 1, wherein the operational circuitry is configured to apply the beat detection method of the ICD of the first configuration and display detected beats via the user interface such that a user can indicate true and false detections in the detected beats.

7. The patient screening device of claim 1, wherein the inputs comprise wireless communication circuits for wirelessly coupling to wireless cutaneous electrodes.

8. The patient screening device of claim 1, wherein the inputs comprise wired connection jacks for coupling to cutaneous electrodes.

9. The patient screening device of claim 1 wherein:
   the operational circuitry is configured to use the user interface to direct a user as to a correct location of cutaneous electrodes on the patient during testing for the ICD of the first configuration;
   the operational circuitry is configured to use the user interface to direct a user to instruct the patient to adopt at least a first posture and a second posture during the step of capturing data; and
   the operational circuitry is configured to apply the beat detection method of the ICD of the first configuration and display detected beats via the user interface such that a user can indicate true and false detections in the detected beats.

10. A method of determining whether a patient is well suited to receiving an implantable cardiac device (ICD) having a first configuration, using an electronic screening device having control circuitry, input circuitry and a user interface, the method comprising:

an electronic screening device capturing data from cutaneous electrodes which have been placed on a patient;

the electronic screening device emulating one or more filtering and detection characteristics of the ICD of the first configuration, including applying a beat detection method that would be used by the ICD of the first configuration, to the captured data;

the electronic screening device determining whether the ICD of the first configuration can accurately analyze cardiac data from the patient and:

if the ICD of the first configuration can accurately analyze cardiac data from the patient, the electronic screening device indicating that the patient is well suited to receiving the ICD of the first configuration; or, if the ICD of the first configuration is not likely to accurately analyze cardiac data from the patient, the electronic screening device determining that the patient should not receive the ICD of the first configuration.

11. The method of claim 10 wherein, if the electronic screening device determines that the patient should not receive the ICD of the first configuration, the method further comprises the patient screening device analyzing signals captured from the patient using emulation of filtering and detection characteristics from an ICD of a second configuration to determine whether the patient is well suited to receive the ICD of the second configuration.

12. The method of claim 10 further comprising the electronic screening device providing, via the user interface, instructions for a user as to a correct location of cutaneous electrodes on the patient during testing for the ICD of the first configuration.

13. The method of claim 10 further comprising the electronic screening device providing, via the user interface, instructions for a user to instruct the patient to adopt at least a first posture and a second posture during the step of capturing data.

14. The method of claim 10 wherein the emulating step includes the electronic screening device applying the beat detection method and generating one or more detected beats, wherein the method further comprises the electronic screening device displaying, via the user interface, detected beats via the user interface such that a user can indicate true and false detections in the detected beats.

15. The method of claim 10 wherein the input circuitry of the electronic screening device comprises a wireless communication circuit for wirelessly coupling to one or more wireless cutaneous electrodes, and the step of the electronic screening device capturing data includes the electronic screening device receiving information from one or more wireless cutaneous electrodes.

16. The method of claim 10, further comprising:

the electronic screening device providing, via the user interface, instructions for a user as to a correct location of cutaneous electrodes on the patient during testing for the ICD of the first configuration; and further comprising the electronic screening device providing, via the user interface, instructions for a user to instruct the patient to adopt at least a first posture and a second posture during the step of capturing data; and wherein the emulating step includes the electronic screening device applying the beat detection method and generating one or more detected beats, wherein the method further comprises the electronic screening device displaying, via the user interface, detected beats via the user interface such that a user can indicate true and false detections in the detected beats.

17. A patient screening device for use in determining whether a patient is well suited to receiving an implantable cardiac device (ICD) having a first configuration, the patient screening device comprising:

interface means for obtaining inputs from and providing information to a user;

input means for receiving data from a plurality of cutaneous electrodes; and processing means for using the interface means and the input means and including emulation means for emulating filtering and detection characteristics of the ICD of the first configuration;

wherein the processing means is configured to:

capture data via the input means from coupled cutaneous electrodes placed on a patient;

filter and perform beat detection on the captured data, including applying a beat detection method that would be used by the ICD of the first configuration;

determine whether the ICD of the first configuration can accurately analyze cardiac data from the patient and:

if the ICD of the first configuration can accurately analyze cardiac data from the patient, determine that the patient is well suited to receiving the ICD of the first configuration; or, if the ICD of the first configuration is not likely to accurately analyze cardiac data from the patient, determine that the patient should not receive the ICD of the first configuration.

18. The patient screening device of claim 17, wherein the processing means is configured to use the interface means to instruct a user as to a correct location of cutaneous electrodes on the patient during testing for the ICD of the first configuration.

19. The patient screening device of claim 17, wherein the processing means is configured to use the interface means to direct a user to instruct the patient to adopt at least a first posture and a second posture during the step of capturing data.

20. The patient screening device of claim 17, wherein the processing means is configured to apply the beat detection method of the ICD of the first configuration to obtain detected beats and use the interface means to display detected beats via the user interface such that a user can indicate true and false detections in the detected beats.

* * * * *